(12) United States Patent
Whitby et al.

(10) Patent No.: US 6,790,408 B2
(45) Date of Patent: Sep. 14, 2004

(54) FRAGRANCE EMITTING DEVICE

(75) Inventors: Paul Howard Whitby, East Yorkshire (GB); Keith Collingwood, Hull (GB); Alain Luciani, Milanes (IT)

(73) Assignee: Reckitt Benckiser (UK) Limited, Slough (GB)

( * ) Notice: Subject to any disclaimer, the term of this patent is extended or adjusted under 35 U.S.C. 154(b) by 0 days.

(21) Appl. No.: 10/047,256

(22) Filed: Jan. 15, 2002

(65) Prior Publication Data

US 2002/0159916 A1 Oct. 31, 2002

Related U.S. Application Data

(63) Continuation of application No. PCT/GB00/02671, filed on Jul. 14, 2000.

(30) Foreign Application Priority Data

Jul. 17, 1999 (GB) ................................................ 9916755

(51) Int. Cl.[7] .............................................. A61L 9/00
(52) U.S. Cl. ............................. 422/4; 261/26; 261/78.2; 261/100; 422/5; 422/120; 422/122; 422/124; 422/125
(58) Field of Search ................................ 422/4, 5, 120, 422/122, 124, 125; 261/26, 78.2, 100

(56) References Cited

U.S. PATENT DOCUMENTS

| | | | | |
|---|---|---|---|---|
| 3,972,473 A | * | 8/1976 | Harrison | 239/34 |
| 4,084,732 A | * | 4/1978 | Dearling | 222/402.17 |
| 4,556,539 A | * | 12/1985 | Spector | 422/125 |
| 4,629,604 A | * | 12/1986 | Spector | 422/124 |
| 4,695,434 A | | 9/1987 | Spector | |
| 4,726,519 A | * | 2/1988 | Muoio | 239/49 |
| 5,314,669 A | * | 5/1994 | Hamilton | 422/305 |
| 5,364,027 A | * | 11/1994 | Kuhn | 239/44 |
| 5,565,148 A | * | 10/1996 | Pendergrass, Jr. | 261/30 |

FOREIGN PATENT DOCUMENTS

| | | |
|---|---|---|
| EP | 0 298 741 A2 | 1/1989 |
| EP | 0 911 041 A2 | 4/1999 |
| EP | 0 911 041 A3 | 9/2000 |
| JP | 09 010292 A | 1/1997 |
| JP | 11000391 | 1/1999 |
| JP | 11 000391 A | 1/1999 |

* cited by examiner

*Primary Examiner*—Krisanne Jastrzab
(74) *Attorney, Agent, or Firm*—Akin Gump Strauss Hauer & Feld, LLP

(57) ABSTRACT

A method and device are provided for preventing the habituation of a fragrance composition. The method and device are adapted to provide to a space, which it is desired to fragrance, a continuous supply of a first fragrance composition and a periodic supply of a second fragrance composition. The fragrance composition(s) may be vaporized by heating and may include deodorant and/or insecticidal compounds.

10 Claims, 2 Drawing Sheets

FRAGRANCE EMITTING DEVICE

CROSS-REFERENCE TO RELATED APPLICATIONS

This application is a continuation of International Application No. PCT/GB00/02671, filed Jul. 14, 2000, which was published in the English language on Jan. 25, 2001, under International Publication No. WO 01/05442 A1 and the disclosure of which is incorporated herein by reference.

BACKGROUND OF THE INVENTION

The present invention relates to a method and a device for preventing the habituation of a fragrance composition.

It is generally known to use an electrical device to evaporate a perfume and/or fragrance composition into a space, particularly a domestic space, e.g., a living room, to provide a pleasant aroma. There are a variety of such devices on sale, for example the Airwick Diffuser Actif® (manufactured by Reckitt Benckiser) or the Ambi-Pur® fragrance diffuser (manufactured by Sara Lee). Generally, these devices consist of a perfume or fragrance source, an electrical heater and a power supply. By the application of heat to the perfume or fragrance source, there will be a constant supply of the perfume or fragrance to the space in which the device is placed.

The problem with this arrangement is that a person occupying the space will quickly become accustomed to the perfume or fragrance and, after a while, will not perceive the fragrance strength as being as intense. This is a well-known phenomenon called habituation. A solution to this problem has been sought.

BRIEF SUMMARY OF THE INVENTION

According to a first aspect of the present invention there is provided a method for preventing the habituation of a fragrance composition, which method comprises providing to a space which it is desired to fragrance two or more fragrance compositions, at least one of which fragrance compositions is provided periodically. According to the invention there is further provided a method wherein a continuous supply of a first fragrance composition and a periodic supply of a second fragrance composition are provided to the space which it is desired to fragrance.

According to a second aspect of the present invention there is provided a device for supplying two or more fragrance compositions to a space which it is desired to fragrance, the device comprising a supply source for periodically supplying at least one of the fragrance compositions to the space. Preferably, the device further comprises a second supply source, which second supply source is adapted to continuously supply a first fragrance composition to the space which it is desired to fragrance.

Each fragrance composition is preferably in the form of a liquid. Suitable solvents for the fragrance components include water, alkyl alcohol, e.g., isopropanol or ethanol, an ether (such as monopropylene glycol methyl ether, dipropylene glycol methel ether and/or tripropylene glycol methyl ether), carbitol or a glycol (such as propyleneglycol or dipropyleneglycol).

When the fragrance composition is in the form of a liquid, it is generally supplied in (or its source is) a container, e.g., a bottle filled with the liquid and provided with a wick. A suitable container is one made from a water/organic solvent insoluble material, which is optionally either a plastic material, for example polypropylene, HDPE (high density polyethylene), PET or Barex or, preferably glass. Suitable wicks are made from natural or synthetic fibrous materials, such as cotton, fiberglass, mineral fibers, cellulose ceramic, graphite or polyester.

Each fragrance composition may additionally comprise a malodor counteractant and/or an insecticide. Preferably, it is the first fragrance composition which may further comprise a malodor counteractant and/or an insecticide.

A suitable fragrance composition for use in the invention comprises one or more fragrant components, such as cedarwood oil, sandalwood oil, bergamot, Bulgarian rose oil, patchouli, myrrh, clove leaf oil, linalol, ethyl alcohol, terpineol, menthol, citronellal, and/or phenyl ethyl alcohol.

The fragrance compositions are preferably chosen such that the two or more fragrance compositions contrast with one another or have different notes. This is particularly important when one fragrance composition is supplied continuously and one is supplied periodically to prevent cross habituation. This is a preferred feature because, if the second fragrance composition is too similar to the first fragrance composition, the periodic supply of the second fragrance composition will not act to counteract the effects of the habituation.

An advantage of the invention is that the problem of habituation is alleviated. In carrying out a preferred embodiment of the method of the invention, a continuous supply of a fragrance composition and a periodic supply of at least one further fragrance composition are supplied to a space which it is desired to fragrance. If the fragrance compositions were continuously supplied, and if there were no periodic supply of a fragrance composition, then a person present in the space would quickly become accustomed to the fragrance composition or compositions. In other words, the person would believe that the strength of the fragrance composition or compositions was decreasing with time. However, when at least one fragrance composition is periodically supplied, the perceived decrease in the strength of the fragrance composition which is continuously supplied is halted. In other words, with the continuous supply of a first fragrance and a pulsed supply of a second fragrance, the strength of the first fragrance is perceived as stronger than it was before the second fragrance composition was supplied.

A suitable deodorant for use in the present invention is one or more aroma and/or non-aroma chemicals, which are known to have an action in reducing the perception of the intensity of malodors, e.g., unsaturated esters, ketones, aldehydes, and/or a fragrant material, e.g., citronella and/or cedarwood oil (which is known to counteract the perception of tobacco malodor).

A suitable insecticide for use in the present invention comprises one or more natural insecticides, such as pyrethroid, nicotinoid, rotenoid and/or one or more synthetic insecticides, e.g., Tetramethrin®, Bioallethrin®, Allethrin®, phenthrin, a dinitrophenol, an organothiocyanate, benzene hexachloride, a polychlorinated cyclic hydrocarbon (e.g., Heptachlor®, Aldrin® and/or Telodrin®, and/or an organophosphorous compound (e.g., tetraethyl pyrophosphate).

Each fragrance composition may further comprise an antioxidant, such as tocopherol, ascorbyl palmitate, butylated toluene, ascorbic acid, tert-butyl hydroquinone, beta carotene and/or a gallate. In addition each active agent may optionally comprise a UV stabilizer, such as Uvinol 400.

In carrying out a preferred embodiment of the present invention, a fragrance composition is generally pulsed from a device which includes a heater, which is adapted to supply heat periodically to the composition which is to be pulsed and thereby vaporize it. When two or more fragrance compositions are to be supplied periodically, the two or more compositions may be pulsed by the use of periodic heaters to the two compositions. Alternatively, if one fragrance composition is to be supplied continuously, then the heater will supply heat continuously to this composition to vaporize it continuously. The other fragrance composition will be heated only periodically to provide pulsed evaporation.

The heater is optionally either a positive temperature coefficient-type (PTC-type) electrical heater or a resistance-based electrical heater. It is preferably a PTC-type electrical heater. The heat output of the heater is preferably suitable to give an operating temperature of from 50 to 120° C., more preferably from 60 to 80° C., most preferably about 70° C.

Each fragrance composition will generally be supplied in a container provided with a wick. The heater will then preferably be in the form of a coil or a ring around the wick. Preferably, the heater is provided with a control which regulates the supply of heat to the fragrance compositions. This is in order that the evaporation rate of the fragrance compositions may be controlled.

Alternatively, a combined fragrance composition may be supplied in a single container with a wick, with the fragrance which is to be pulsed having a higher vaporization temperature than the fragrance which is to be continuously released. Supply of heat to the wick will vaporize the first fragrance which is to be supplied continuously. The second fragrance may then be vaporized by periodically increasing the heat supply to the wick.

The device according to the second aspect of the present invention is preferably an electrical device. The electrical power supply is optionally either in the form of one or more electrical batteries or, preferably, the electrical device is adapted to be connected to an electrical power supply, e.g., a domestic mains socket. The device is preferably provided with an actuator, e.g. a switch, to control operation of the device.

The periodic supply of heat to release the fragrance composition is preferably achieved by providing the device and particularly the heater with a controller. The controller is preferably in the form of an electronic circuit, e.g. a printed circuit board. The controller is preferably an astable electronic timing circuit, for example one based on a 555 integrated circuit or an inverting Schmitt trigger (e.g. a 74LS14 integrated circuit). The controller is preferably arranged such that that a power supply is connected to the heater for a short period of time at a frequency of from 1 to 5 times an hour. This short period of time is preferably from 15 seconds, more preferably from 30 seconds to, preferably, 15 minutes, more preferably 2, 4, 6, 8, or 10 minutes, with appropriate intervals of time therebetween.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
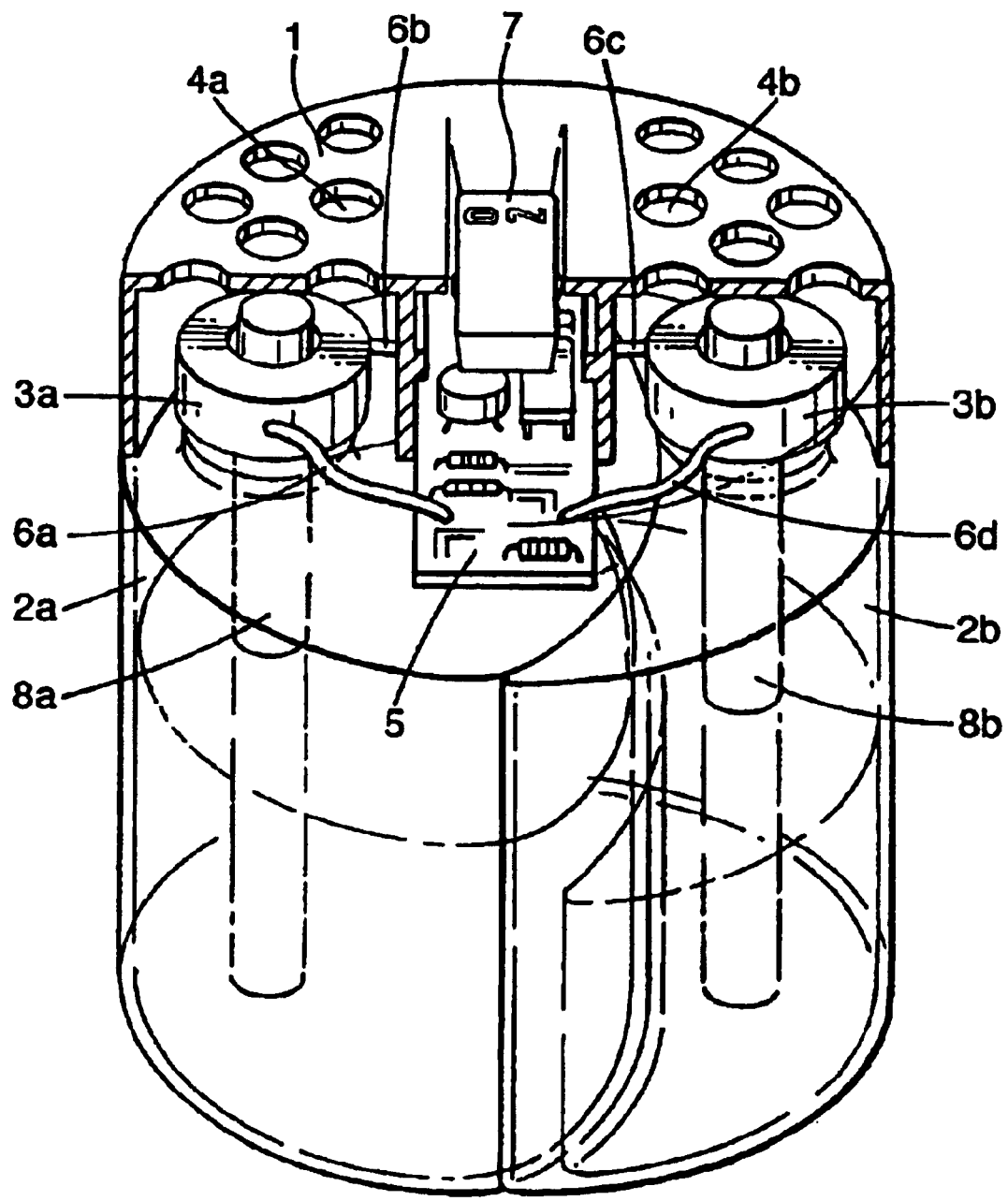
FIG. 1 is a perspective view, partially in section, of a device for use in the method of the present invention, which is adapted to supply a first fragrance continuously and to pulse a second fragrance.

Referring now to FIG. 1, there is shown a device for use in the method of the invention which comprises a housing 1 which is shown in section. Housing 1 is made from a substantially non-deformable heat-resistant material such as a thermoplastic resin containing a flame retardant agent, e.g. polypropylene, polyethylene and/or an acrylonitrile/butadiene/styrene copolymer.

Housing 1 is adapted to support containers 2a and 2b and heaters 3a and 3b. Heaters 3a and 3b are annular electrical heaters and are arranged vertically above containers 2a and 2b. Containers 2a and 2b are made from a water/organic solvent insoluble material.

Container 2a is filled with a first fragrance composition and container 2b is filled with a second fragrance composition. Containers 2a and 2b are provided with wicks 8a and 8b, which contact the first and second fragrance compositions, respectively. Wicks 8a and 8b are made from natural or synthetic fibrous materials and extend from the bottom of containers 2a and 2b, substantially coaxially through annular heaters 3a and 3b to a point vertically just above the heaters 3a and 3b. Thus, the wicks 8a and 8b cause the fragrance compositions to flow from the containers 2a and 2b to the levels of the heaters 3a and 3b. Housing 1 has holes 4a and 4b which are disposed substantially vertically above containers 2a and 2b, respectively.

Holes 4a and 4b allow vapor communication between the wicks 8a and 8b and the outside (ambient environment). Housing 1 is also adapted to support controller 5 and is adapted to allow electrical conductors 6a, 6b, 6c and 6d to link controller 5 with heaters 3a and 3b. Housing 1 is further adapted to support actuator 7 and is also adapted to allow actuator 7 to be electrically connected to the controller 5. Housing 1 is also adapted to provide controller 5 with a source of electrical power (not shown). Actuator 7 is movable between a first operating position and a second non-operating position. Controller 5 is arranged so that when the device is in operation (i.e., when circuit 5 is connected to a source of electrical power and actuator 7 is in the first operating position), electrical power is supplied continuously to heater 3a and periodically to heater 3b. The electrical power provided continuously to the heater 3a causes the heater 3a to heat the wick 8a which is saturated with the first fragrance composition, so that the fragrance composition vaporizes. The vapor of the first fragrance composition provided by heating the wick 8a is able to escape to the ambient environment through holes 4a.

Figure 2:
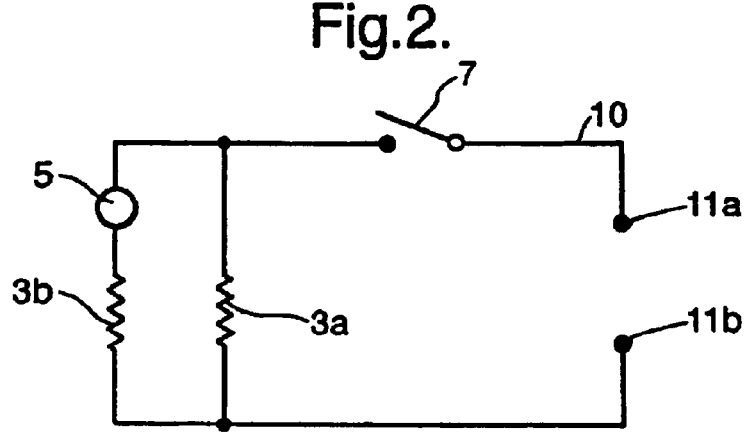
FIG. 2 is a schematic diagram of an electrical circuitry used in respect of the device of FIG. 1.

Referring now to FIG. 2, there is shown an electrical circuit 10 suitable for use with the device of FIG. 1. The electrical circuit comprises connectors 11a and 11b which allow the electrical circuit to be connected to an electrical power supply, an actuator 7, heaters 3a and 3b, and a controller 5.

Figure 3:
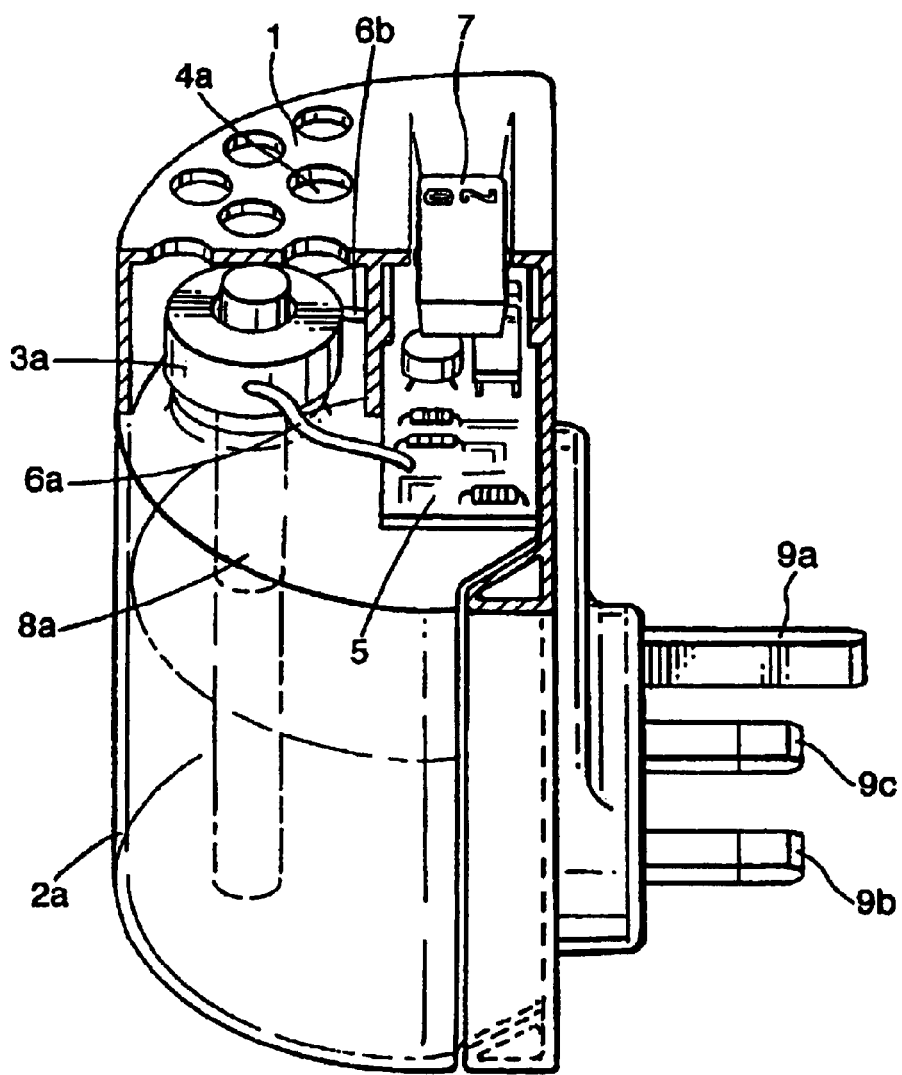
FIG. 3 is a side perspective view, partially in section, of a device for use in the method of the present invention, which is adapted to pulse with a single fragrance.

Referring to FIG. 3, there is shown a side projection of a device according to the invention, which comprises a housing 1 which supports a single container 2a and an actuator 7. Container 2a is filled with a fragrance composition and is provided with a wick 8a. In the embodiment of the invention depicted in FIG. 3, connector 9a, 9b and 9c corresponding to the pins of an electrical plug enable the device to be provided with a source of electrical power. The connector 9a, 9b and 9c enable the device to fit into a UK domestic mains socket. Thus, connector 9a is an earth (ground) pin, connector 9b is a neutral pin and connector 9c is a live pin. The arrangement of the pins and the shape of the rear section of the housing may be changed according to the local design of main sockets. The device illustrated in FIG. 3 may be used with an electrical circuit similar to that illustrated in FIG. 2, but with a single heater.

The present invention will be further described with reference to the following non-limiting Examples.

EXAMPLE 1

An experiment was carried out to assess the perceived strength of a continuous core fragrance (ginger flowers) boosted by pulses of another fragrance (pomme) for 6 minutes at 15 minutes intervals. The test was conducted in 28m$^3$ temperature and humidity controlled booths (20° C. and 55% R/H).

A panel of 13 testers was asked to assess the perceived fragrance strength of the continuous core fragrance over a period of 42 minutes, the assessment being rated every minute according to a preordained scale. The perceived fragrance of the ginger flowers was constant for the duration of the assessment.

EXAMPLE 2

An experiment similar to that described in Example 1 was compared with a control experiment in which the core fragrance (ginger flowers) was supplied to the booths and an experiment in which the core fragrance was applied continuously with pulses of pomme fragrance. Pulsing with the pomme fragrance for two or six minutes at fifteen-minute intervals with constant ginger flowers fragrance produced a higher perceived strength than constant ginger flowers alone. The experiment with six-minute pulsing showed a lesser decline in perceived fragrance than pulsing for two minutes.

EXAMPLE 3

Following the general protocol of Example 1, an experiment was carried out to assess the perceived strength of a single fragrance (freesia and magnolia) pulsed for two minutes with a rest period of two minutes between the end of one pulse and the beginning of the next. The assessment was carried out in the manner as described in Example 1 for a total of 46 minutes. The pulsing maintained the perceived fragrance strength at a constant level throughout the duration of the assessment.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method for preventing the habituation of a fragrance composition, which method comprises providing to a space which it is desired to fragrance a continuous supply of a first fragrance composition and a controlled periodic supply of a different second fragrance composition.

2. The method as claimed in claim 1, wherein the periodic supply of the second fragrance composition is at a frequency of from 1 to 5 per hour.

3. The method as claimed in claim 1, wherein a pulsing time for the periodic supply is 2, 4, 5, 6, 8 or 10 minutes with intervals between the pulses of the same or different times.

4. The method as claimed in claim 1, wherein the periodic supply of the second fragrance composition to the space is provided by periodically heating the second fragrance composition in order to vaporize it.

5. The method as claimed in claim 1, wherein at least one of the fragrance compositions comprises at least one of a deodorant and an insecticidal compound.

6. The method as claimed in claim 1, wherein at least one of the fragrance compositions is in a liquid form.

7. The method as claimed in claim 6, wherein each fragrance composition is supplied in a container provided with a wick.

8. The method as claimed in claim 7, wherein a heater surrounds the wick of each container.

9. The method as claimed in claim 8, wherein at least one heater is operated electrically.

10. A device for preventing the habituation of a fragrance composition, the device being adapted to supply at least two fragrance compositions to a space which it is desired to fragrance, the device comprising a first supply source for continuously supplying a first fragrance composition to the space and a second supply source and a controller for periodically supplying a second different fragrance composition to the space.

* * * * *